United States Patent
Sharp et al.

(10) Patent No.: US 6,598,463 B2
(45) Date of Patent: Jul. 29, 2003

(54) METHOD FOR DETERMINING GAS ACCUMULATION RATES

(76) Inventors: Kenneth George Sharp, 164 Hamilton Rd., Landenberg, PA (US) 19350; Dennis George Swartzfager, 2 Star Pine Cir., Wilmington, DE (US) 19808; John Blase Zucaro, 30 W. Kapok Dr., Newark, DE (US) 19702

( * ) Notice: Subject to any disclaimer, the term of this patent is extended or adjusted under 35 U.S.C. 154(b) by 0 days.

(21) Appl. No.: 10/128,710

(22) Filed: Apr. 22, 2002

(65) Prior Publication Data

US 2002/0162384 A1 Nov. 7, 2002

Related U.S. Application Data

(60) Provisional application No. 60/288,216, filed on May 2, 2001.

(51) Int. Cl.[7] ............................................. G01N 15/08
(52) U.S. Cl. ........................................................ 73/38
(58) Field of Search ................................ 73/38, 49.2 R, 73/49.3, 52

(56) References Cited

U.S. PATENT DOCUMENTS

| | | | | |
|---|---|---|---|---|
| 3,958,448 A | * | 5/1976 | Willis et al. ................. | 73/37 |
| 4,047,422 A | * | 9/1977 | Lyssy ............................ | 73/38 |
| 5,497,654 A | * | 3/1996 | Lehmann ..................... | 73/49.3 |
| 5,857,580 A | * | 1/1999 | Iidaka ......................... | 215/256 |
| 6,422,063 B1 | * | 7/2002 | Anantheswaran et al. ..... | 73/38 |
| 6,478,853 B1 | * | 11/2002 | Hara et al. .................... | 95/56 |

FOREIGN PATENT DOCUMENTS

DE                      119472             2/1975

* cited by examiner

*Primary Examiner*—Helen Kwok
*Assistant Examiner*—Tamiko Bellamy

(57) ABSTRACT

The Invention concerns an apparatus for and method for the simultaneous determination of permeation rate through and desorption rate from a polymeric specimen, the method comprising sealingly separating a first volume from a second volume with a specimen to be tested, said specimen being suffused with a first isotope of a gas or vapor;

introducing in said first volume a second isotope of said gas or vapor, said second isotope being detectably distinguishable from said first isotope;

in said second volume, adjusting the partial pressure of both said isotopes of said gas or vapor to a negligible value compared to that of said second isotope of said gas or vapor in said first volume;

and, distinguishably detecting the concentration of each said diffusing isotope of said permeant in said second volume.

16 Claims, 4 Drawing Sheets

METHOD FOR DETERMINING GAS ACCUMULATION RATES

FIELD OF THE INVENTION

Disclosed is a method for determining the accumulation rate of gases in an enclosed volume.

TECHNICAL BACKGROUND OF THE INVENTION

An important area of commerce is the packaging of goods subject to deterioration, such as foods, cosmetics, medicines, and the like. Deterioration often results from the diffusion of gases through the packaging material. This diffusion may be in the form of the loss of carbonation in a beverage, the loss of fragrance in a cosmetic, or the accumulation of oxygen or other reactive permeants into the package causing the contents thereof to undergo undesired oxidation or other reaction. Goods packaged in plastics are particularly susceptible to diffusion-related deterioration.

Widespread research has been undertaken to identify methods for reducing the deterioration of goods packaged in plastics by interfering with the diffusive transport of various permeants through the packaging material. In order to make those advances, it is necessary to have quick, accurate, and reproducible methods for characterizing the diffusive processes which contribute to product deterioration. One particularly difficult problem is presented when the permeant of interest is present at high concentrations within the packaging material to be characterized.

This is the situation, for example, when the infusion of oxygen into a plastic package is to be characterized. Oxygen exhibits quite high solubility in many plastics used in the packaging industry. Because oxygen is present in the ambient atmosphere, any such oxygen-soluble material in commercial use will be suffused with oxygen. In such a case, the infusion rate of oxygen into an initially oxygen-free package will be governed both by the rate of permeation of atmospheric oxygen through the packaging material, and by the rate of oxygen desorption from the packaging material. Any effort to control oxygen infusion into the package must take account of both processes, and it is therefore necessary to characterize each process independently.

The present invention provides a method for the separate, simultaneous characterization of desorption and permeation using a single specimen.

Representative of the methods most commonly employed in the art for measuring permeation rates is that for determining the oxygen permeation rate of plastics as described in ASTM D3958. In this procedure one side of a film or container is subject to a constant partial pressure of oxygen while the other side of the film or container is swept with a continuous stream of nitrogen. Oxygen diffusing into the nitrogen stream is detected by some quantitative method to give the rate of oxygen infusion. The Ox-Tran series of test stands manufactured by Modem Controls, Inc., Minneapolis, Minn., is commonly employed for oxygen permeability measurements; the detector is a fuel cell.

When the test specimen is suffused with oxygen, there is no known practical method for separating the oxygen desorption contribution to the total rate of oxygen accumulation from the oxygen permeation contribution. The problem is greatly aggravated when the sample to be characterized is in some complex shape such as that of a bottle where the introduction of inhomogeneities in thickness and crystallinity may be inherent in the process of formation. In the current state of the art, the permeation contribution is determined simply by waiting to take data until the desorption contribution becomes negligible. In other words, meaningful permeation data cannot be taken until the specimen has been outgassed. That point is usually determined to be the point at which the rate of permeant accumulation in the previously permeant free volume becomes linear with time. In certain circumstances of current interest, this may take as long as several weeks.

The desorption component may be determined by subjecting a specimen to vacuum or an inert atmosphere on both sides and determining the rate of degassing. That is to say, it must be performed with the exclusion of any atmospheric permeant contribution.

In a different approach, Hanke, East German Patent 119472, determines the lag time for oxygen diffusion in construction materials by sealing a specimen between two chambers which are maintained at equal oxygen partial pressures, introducing a rare isotopic species on one side of the specimen, and observing the time required to detect the species on the other side. $^{18}O_2$, $^{15}N_2$, and $^{85}Kr$, which is radioactive, are all isotopic species employed in Hanke. While Hanke's method is suitable for analyzing permeation through the specimen, it is completely unsuitable for the simultaneous determination of the permation and desorption rates. In Hanke's case, oxygen desorption was neither of concern, nor was it likely to be of significance.

SUMMARY OF THE INVENTION

The present invention provides a method for the simultaneous determination of permeation rate through and desorption rate from a polymeric specimen, the method comprising:

sealingly separating a first volume from a second volume with a specimen to be tested, said specimen being suffused with a first isotope of a gas or vapor;

introducing in said first volume a second isotope of said gas or vapor, said second isotope being detectably distinguishable from said first isotope;

in said second volume, adjusting the partial pressure of both said isotopes of said gas or vapor to a negligible value compared to that of said second isotope of said gas or vapor in said first volume;

and, distinguishably detecting the concentration of each said diffusing isotope of said permeant in said second volume.

Further provided in the present invention is an apparatus fluid seal adapted for use in testing gas permeability of plastic bottles, the apparatus comprising:

a cylinder having an interior wall, a first end, and a second end, the ends being open;

a plug having a surface said plug disposed in said first end of said cylinder in such manner that a gap exists between the surface of the plug and the interior wall of the cylinder;

a first seal disposed within said gap proximate to said first end, and a second seal disposed within said gap proximate to said second end, said seals, said wall, and said plug surface defining a volume; and, a means provided within said plug permitting introduction and removal of fluid within said defined volume.

DETAILED DESCRIPTION OF THE INVENTION

Figure 1:
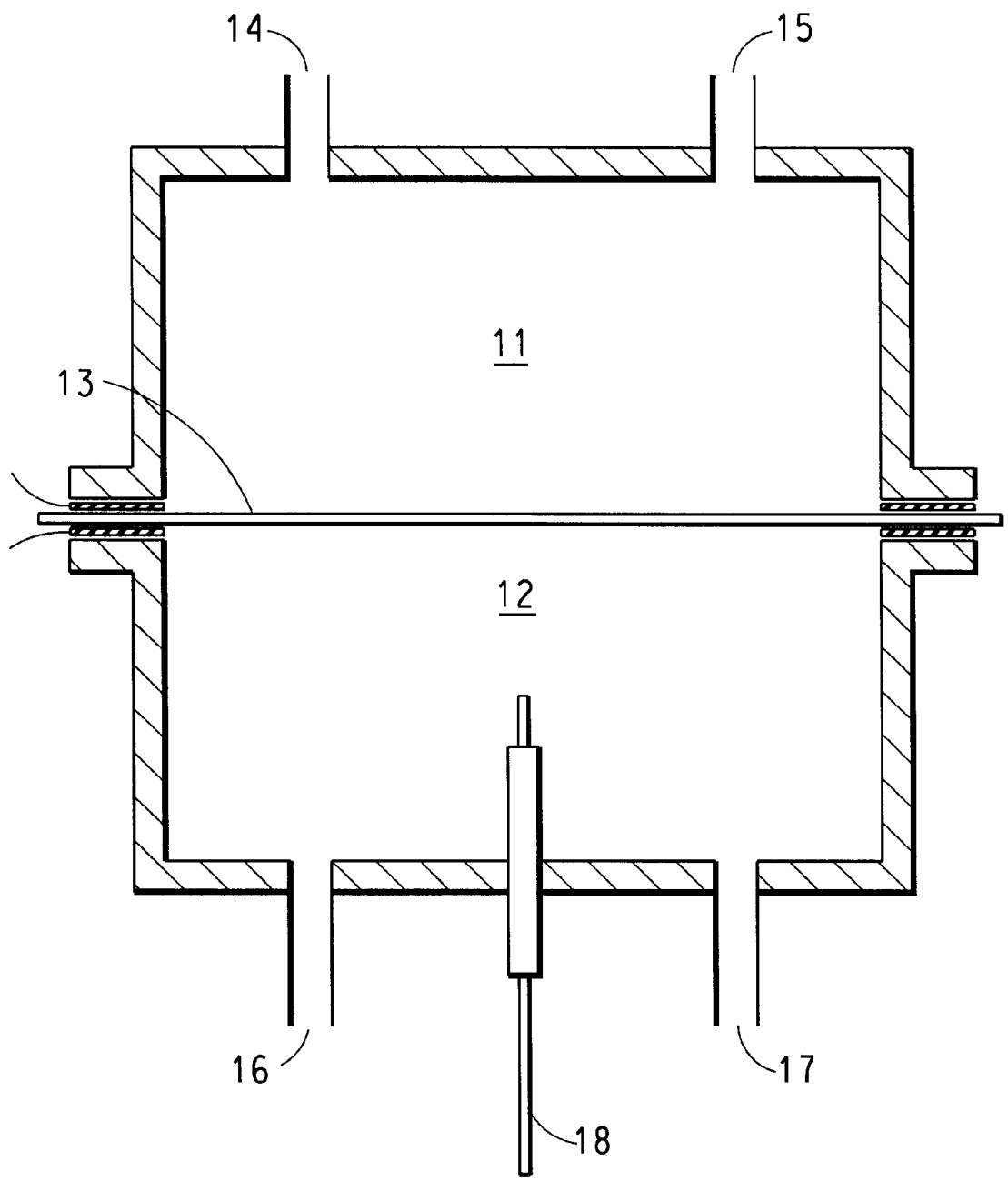
FIG. 1 shows a test cell of circular cross-section suitable for measurement of flat, thin films.

In the present invention, the test specimen is disposed between two volumes in such a manner as to isolate them from one another except for diffusive transport through the test specimen.

In the practice of the present invention, a specimen in the form of a shaped article, preferably a flat film or sheet, or a container, which specimen is suffused with a first isotope of a gas or vapor, is disposed between a first and second volume. A second isotope of the gas or vapor, detectably distinguishable from said first isotope, is introduced into the first volume. Meanwhile, preferably, the partial pressure of both said isotopes in the second volume is reduced effectively to zero. Said second volume is then provided with a pressure of an inert gas equal to the pressure in the first volume. The second volume may be provided with a continuous flux of inert gas which serves to convey any of either said isotope which diffuses into said second volume to a detection means which quantitatively distinguishes between the two said isotopes, or the atmosphere of the second volume may be sampled at defined intervals for analysis by the detection means. The time dependence of the concentration of said first isotope in said second volume is indicative of the desorption rate from the specimen. The time dependence of the concentration of said second isotope in said second volume is indicative of the permeation rate through the specimen. Typically the concentrations are determined using the concentration of the inert gas in the second volume used as a standard.

One of skill in the art will appreciate that temperature variability during measurement is a source of potential error. As a general rule, it is highly desirable to maintain the apparatus at constant temperature for the duration of the measurement period. In the practice of the present invention it has been found that precision of ca. 1–2% could be maintained when temperature variability was on the order of ±1 centigrade degree.

It is not an absolute requirement for the practice of the invention that the partial pressure of the permeant in the second volume be reduced to zero prior to the commencement of the measurement, but it is highly preferred. For the purposes herein, zero partial pressure means that the partial pressure is sufficiently low that it need not be taken into account in the subsequent data analysis. It will be clear to one of skill in the art that a suitable partial pressure in the second volume depends upon the desired precision of measurement. The partial pressure in the second volume may be reduced to the desired level by any of several means in the art such as by the application of vacuum pumps of all varieties, or by purging with inert gas.

The measurement according to the present invention is advantageously performed at pressures slightly in excess of atmospheric pressure, typically on the order of ca. 30 torr above atmospheric pressure. The measurements may be performed at pressures above or below atmospheric pressure as well.

It is however important to maintain approximately equal pressures in the two volumes. Excessive pressure differentials may cause distortion of the test specimen and distort the results obtained as well. Therefore it is preferred to both evacuate and pressurize the two volumes simultaneously, in such a manner that the pressure differential never exceeds 20 torr.

While the method of the invention may be employed to determine the permeation rate of any gas or vapor of interest to the practitioner hereof, the method herein is of highest utility in those circumstances under which the gas or vapor of interest is also suffused within the test specimen at sufficiently high concentration and mobility that it will contribute significantly to the total rate of gaseous accumulation in the second volume.

The method of the invention is most advantageous when the permeability of the sample is very low. Containers and bottles for oxygen sensitive foods and beverages with a desired shelf life greater than a few months are prime examples of the types of samples for which the method is most applicable.

The method of the present invention achieves the objective of simultaneous determination of desorption rate and permeation rate of the same gas or vapor by using as the gas or vapor introduced into the first volume an isotope of the gas or vapor different from the one the test specimen is suffused with. Then in order to distinguish between the respective contributions of desorption and permeation to the total rate of accumulation of the gas or vapor into the second volume, the concentration as a function of time of each of the isotopes is simultaneously or sequentially determined by a quantitative detection means which can distinguish between the two isotopes. The precision of the method of the invention is limited by the effect of the isotopic weight difference on the diffusion coefficient of the permeating gas which according to a theoretical analysis well-known in the art varies as the square root of the mass ratio of the isotopes, and by the precision of the measuring instruments themselves.

Suitable methods for determining the concentrations of the two isotopes include mass spectrometry, raman spectroscopy, infrared spectroscopy, microwave spectroscopy, nuclear magnetic resonance spectroscopy, and radiological detection methods, though the applicability of a given method will depend upon the particular gas or vapor employed. Mass spectrometry is preferred.

One of skill in the art will understand that the method hereof may be practiced without actually independently measuring the respective rates of accumulation in the second volume of the two isotopic species, but of course information will be lost.

As an example of the utility of the method, in a preferred embodiment the method of the invention is employed to determine the rate of accumulation of oxygen in a plastic bottle which is being considered as a candidate beer bottle. It has been found in the beer making art that very low concentrations of oxygen will damage the flavor of beer. Oxygen, which is pervasive in the atmosphere, exhibits considerable solubility in most plastics, such as polyethylene terephthalate (PET), commonly employed for bottles. Thus a bottle sealed under conditions whereunder effectively all the oxygen has been removed will experience oxygen accumulation at a rate determined not only by the diffusive transport of oxygen from the atmosphere through the bottle, but also by desorption of dissolved oxygen from the material of which the bottle is made.

In one embodiment of the invention, the method of the present invention is employed by a researcher who seeks to develop methods for minimizing the exposure of beer or other goods to oxygen. In another embodiment, the method of the present invention is used as a quality control technique to identify and quantify defects in bottles to be employed in critical applications. In either embodiment, the method of the present invention provides a rapid, single-step method for distinguishing the desorption process from the permeation process.

Figure 2:
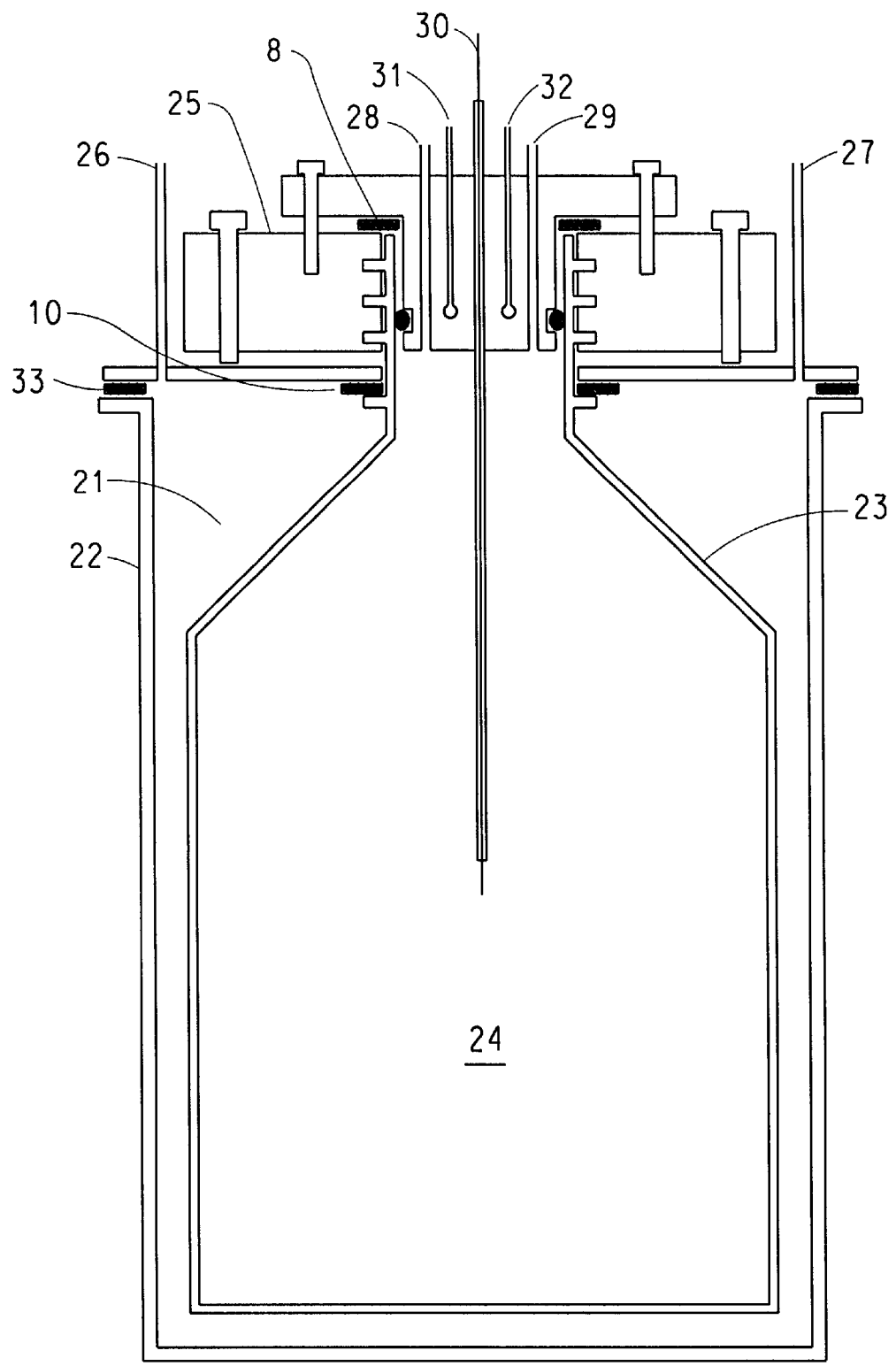
FIG. 2 shows a test cell suitable for measurement of bottles of one particular shape.

The method of the invention may be practiced, but is not limited to, utilizing the test cells shown in FIGS. 1 and 2.

FIG. 1 shows a schematic of one embodiment of an apparatus suitable for practicing the method of the invention on a flat test specimen such as a film or sheet. The apparatus comprises a first volume, 11, and a second volume, 12, with a test specimen, 13 sealingly disposed between them. Any manner of sealing is suitable so long as it meets the requirements of the particular test protocol for leakage. Sealing can be achieved by the use of gaskets, o-rings, or by self-gasketing between highly polished matched surfaces. In the case of extreme sensitivity, it may be necessary to isolate the sealing interface from the ambient atmosphere. The first volume is provided with an inlet, 14, to permit introduction of the permeant, and an outlet, 15, to a vacuum pump or bleed valve to permit evacuation or purging of the first volume, prior to introduction of the permeant. The second volume is likewise provided with both a second inlet, 16, and an outlet, 17 for purging the second volume, and a micro-sampling capillary, 18, leading to the detection means.

FIG. 2 shows an apparatus suitable for testing a bottle or other container. In this case the first volume, 21, is the volume between the inside wall of the test chamber, 22, and the outside wall of the bottle, 23, to be tested. The second volume, 24, is the interior volume of the bottle, 23. The second volume is isolated from the ambient atmosphere by a seal cap, 25, with a double seal 10 and 33 at the mouth of the bottle. The first volume, 21, is provided with an inlet, 26, to permit introduction of the permeant and an outlet, 27, for evacuating or purging the first volume. The second volume is likewise provide with both an inlet, 28, and outlet, 29, and also a micro-sampling capillary, 30, leading to the detector. Inlet, 31, and outlet, 32, provide a means of purging the double seal of the sealing cap, 25, at any time.

Although not shown in the Figures, it will be understood by one of ordinary skill in the art that each inlet and outlet may be equipped with a shut-off valve, and that the sampling capillary may similarly be equipped with a valve so that measurement may be performed either continuously or at discrete intervals.

The thickness of the seal and the material from which it is fabricated is not critical unless the permeability of the specimen is very low. In such cases the seals are best formed with a thin (5–10 micrometer) layer of high vacuum grease or an appropriate adhesive to minimize the ratio of the exposed seal area to the area of the film.

Alternatively, as shown in the particular embodiment of FIG. 2, a novel fluid seal is employed which is particularly advantageous for testing bottles exhibiting very high barrier properties where leakage at or diffusion through the seal, though low by ordinary standards, may still be sufficient to distort the results.

The fluid seal of the invention comprises a cylinder having an interior wall, a first end, and a second end, the ends being open;

a plug having a surface said plug disposed in said first end of said cylinder in such manner that a gap exists between the surface of the plug and the interior wall of the cylinder;

a first seal disposed within said gap proximate to said first end, and a second seal disposed within said gap proximate to said second end, said seals, said wall, and said plug surface defining a volume; and, a means provided within said plug permitting introduction and removal of fluid within said defined volume.

Preferably the cylinder is the neck of a bottle, the first end being the mouth of the bottle. Also preferably the means permitting introduction and removal of fluid within the defined volume is a channel opening into the defined volume between the seals leading through the plug and leading to a vacuum pump or a supply of an inert fluid. Other means for introducing or removing fluid are also feasible. For example, in place of a channel, the plug may be fabricated of a porous material through which diffusive transport may be effected.

Preferably the fluid is a gas but it may be a liquid when appropriate to some particular use. In the practice of the invention, the fluid employed is not associated with any of the measurements being made on the system. For example, for the measurement of oxygen barrier according to the method of the invention, the fluid would not be oxygen, and, if argon is used as a standard, then it would not be argon.

In the practice of the invention, it is satisfactory to evacuate the defined volume between the seals, and then to pressurize the volume with an inert gas. The thus pressurized volume may contain a static gas atmosphere, or the volume may be continuous purged. Preferably the pressure within the volume between the seals will be closely comparable to that within the bottle being tested, and slightly above atmospheric pressure.

The seals may be of any suitable sealing material, generally elastomeric or rubbery in nature. Preferably they are of a fluorelastomeric material such as Viton® fluoroelastomer available from the DuPont Company, Wilmington Del.

Figure 3:
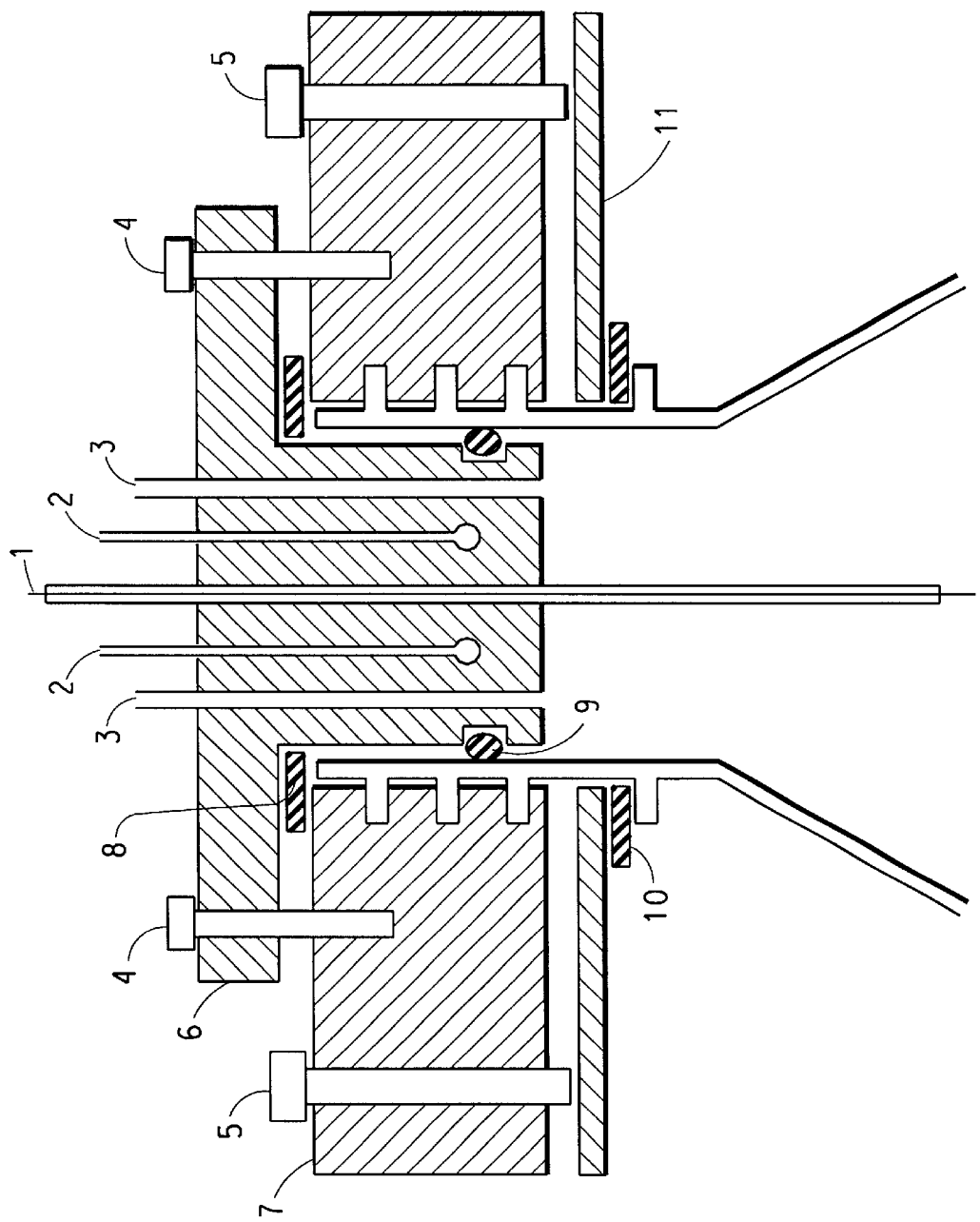
FIG. 3 shows one embodiment of the fluid seal of the invention.

A preferred fluid seal of the invention is depicted in FIG. 3. In FIG. 3, the plug is stainless steel cap, 6, which is provided not only with the features of the fluid seal of the invention but also with the means for controlling and sampling the atmosphere in the bottle being characterized according the method herein. Also shown is a third seal, which is preferred in the embodiment shown. A silica capillary tube, 1, leads from the interior of the bottle to a gas chromatograph sampling valve connected to a detection means, an inlet and outlet, 2, are provided for purging between seals, an inlet and outlet, 3, are provided for evacuating/backfilling the bottle, one of 3 sealing screws is shown, 4, for securing the exterior cap seal, 8, and one of 3 jacking screws is shown, 5, which compresses seal 10. Also shown is a stainless steel seal cap, 6, a threaded, stainless steel jacking ring, 7, an elastomeric exterior cap seal, 8, an elastomeric interior cap seal, 9, an elastomeric bottle seal, 10, and a stainless steel sealing plate, 11.

In the most preferred embodiment of the method of the present invention, a candidate bottle is placed into a cell similar to that in FIG. 2. The bottle is surrounded by a glass chamber of approximately twice the volume of the bottle. The bottle and surrounding annular space are evacuated, then the bottle is filled to atmospheric pressure with nitrogen containing approximately 200 ppm argon or other reference gas. Simultaneously, in order to prevent distortion of the bottle, the annular space is filled to atmospheric pressure with an approximately 1:1 mixture of $^{18}O_2$ and the same nitrogen/argon mixture used to fill the bottle. The contents of the bottle are sampled periodically by removing a very small quantity through a gas chromatographic sampling valve leading to the ion source of a quadrupole mass spectrometer (QMS). During the experiment, the concentrations of $^{16}O_2$, $^{18}O_2$ and argon at masses 32, 36 and 40, respectively, are monitored. The absolute concentration of both oxygen species in the bottle is determined from the ratio of the signal for those species to that of the argon standard (suitably adjusted for the relative sensitivity of the mass spectrometric detector to the species in question). No preconditioning with a lengthy nitrogen purge is necessary.

The method of the invention is applicable to the determination of the rate of accumulation of atmospheric components besides oxygen. Transport of both water vapor and carbon dioxide are also of importance in the packaging industry. The method herein may be applied equally well, for example, for the isotopic pairs $H_2^{18}O/H_2^{16}O, C^{18}O_2/C^{16}O_2$, and $^{15}N_2$. One of skill in the art will appreciate that in the case of $CO_2$ the $^{13}C$ or $^{14}C$ isotopes can be used in combination with the common $^{12}C$ isotope with similar beneficial results.

The practice of the invention is not limited however to problems of interest to the packaging interest, but is indeed widely applicable. Thus it can be equally applied to $N_2$, for example were it desired to characterize the accumulation of nitrogen within a membrane-sealed chamber employed in deep-sea diving. In a further extension of the invention, the method may be used equally effectively in situations wherein the ambient atmosphere atmosphere of interest is not air, but where it is desired to understand the mechanism of diffusive transport of a gas or vapor present in the atmosphere of use for a film, membrane, sheet, or container when the gas or vapor is soluble within the material of interest. Thus, so long as there are available isotopes, methods for handling the samples, equipment, and isotopes, and methods for distinguishing the isotopes, the applicability of the method herein is not limited. Isotopically distinguishable species suitable for use in the method of the invention include, but are not limited to, $CH_4$, Ar, $SO_2$, $CF_2Cl_2$, CO, $H_2S$, $H_2CO$, $Cl_2$, and $O_3$.

The invention is further described in the following specific embodiments.

EXAMPLE

Example 1

Permeability of a Polyester Bottle

A commercially available blow molded polyethylene terephthalate bottle with an internal volume of 540 ml was secured into an apparatus according to FIG. 2. Both the bottle and annular space were evacuated to a pressure of 200 mtorr using a mechanical roughing pump de-gassed for a total of 60 min. Then the bottle was filled with dry nitrogen containing 220 ppm argon and the annular space simultaneously filled with an equal pressure of a mixture of 50% $^{18}O_2$ and 50% the same nitrogen/argon mixture as added to the bottle. Both chambers were pressurized to ca 2% above atmospheric pressure. The ambient temperature was approximately 26±1° C. over the duration of the measurement. Samples were acquired at approximately hourly intervals for the first forty hours, then less frequently for the remaining 120 hours of the measurement. Sample acquisition was accomplished by manually opening a Valco Instrument Company, (Houston Tex.) capillary gas chromatograph sampling valve on the inside of the bottle, and removing 0.25 ml. The thus removed sample was conveyed to a UTI, (California) Model 100C quadrapole mass spectrometer.

Figure 4:
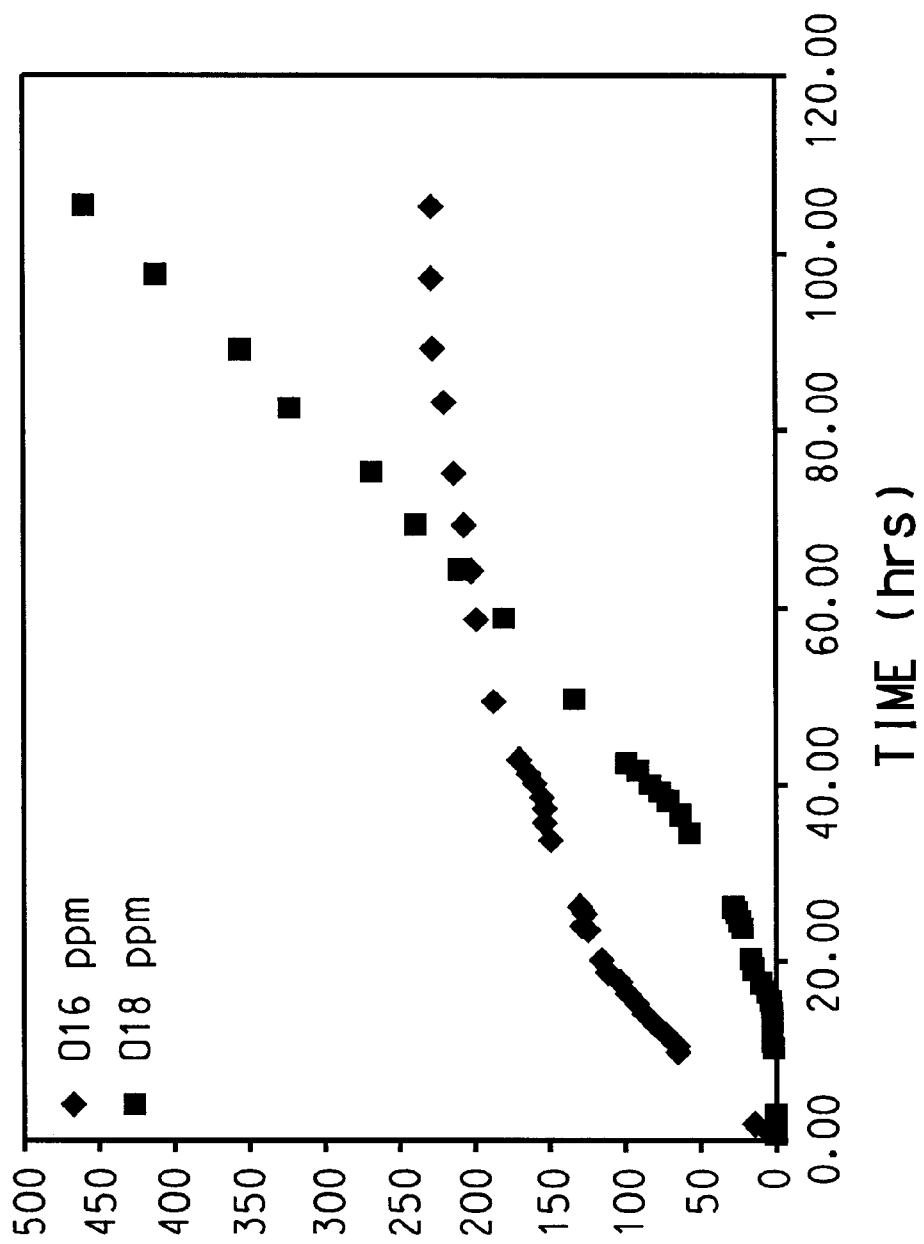
FIG. 4 shows the permeation and desorption curves obtained according to the invention as exemplified in the specific embodiment hereinbelow.

FIG. 4 shows the concentration of both $^{16}O_2$ and $^{18}O_2$ as a function of time. The oxygen permeability attributes of the sample was determined from the $^{18}O_2$ curve while the oxygen desorption attributes were determined from the $^{16}O_2$ curve.

What is claimed is:

1. A method or the simultaneous determination of permeation rate of a gas or vapor permeant through and desorption rate of said permeant from a polymeric specimen, the method comprising sealingly separating a first volume from a second volume with a test specimen suffused with a first isotope of a gas or vapor;

introducing in said first volume a second isotope of said gas or vapor, said second isotope being detectably distinguishable from said first isotope;

in said second volume, adjusting the partial pressure of both said isotopes of said gas or vapor to a negligible value compared to that of said second isotope of said gas or vapor in said first volume;

providing said second volume with a means for conveying said gas or vapor diffusing thereinto to a detection means capable of quantitatively distinguishing between said first and said second isotopes of said gas or vapor;

and, distinguishably detecting the concentration of each of said diffusing ant in said second volume.

2. The method of claim 1 wherein said specimen is in the form of a bottle.

3. The method of claim 1 wherein said first isotope is selected from the group consisting of of $H_2^{16}O$, $^{16}O_2$, $^{12}C^{16}O_2$, and $^{14}N_2$.

4. The method of claim 1 wherein said second isotope is selected form the group consisting of $H_2^{18}$, $^{18}O_2$, $^{13}C^{16}O_2$, $^{14}C^{16}O_2$, $^{12}C^{18}O_2$, and $^{15}N_2$.

5. The method of claim 1 wherein said first isotope is $^{16}O_2$ and said second isotope is $^{18}O_2$.

6. The method of claim 1 wherein said detection means is selected from the group consisting of mass spectrometry, raman spectroscopy, infrared spectroscopy, microwave spectroscopy, nuclear magnetic resonance spectroscopy, and radiological detection methods.

7. The method of claim 6 wherein said detection means is mass spectrometry.

8. The method of claim 1 wherein said second volume further comprises a pressure of an inert gas.

9. The method of claim 8 wherein said inert gas comprises Argon.

10. The method of claim 2 wherein the bottle comprises polyester.

11. The method of claim 10 wherein the bottle comprises polyethylene terephthalate.

12. A fluid seal comprising a cylinder having an interior wall, a first end, and a second end, the ends being open;

a plug having a surface said plug disposed in said first end of said cylinder in such manner that a gap exists between the surface of the plug and the interior wall of the cylinder;

a first seal disposed within said gap proximate to said first end, and a second seal disposed within said gap proximate to said second end, said seals, said wall, and said plug surface defining a volume; and, a means provided within said plug permitting introduction and removal of fluid within said defined volume.

13. The seal of claim 12 wherein the cylinder is the neck of a bottle and the first end is the mouth of the bottle.

14. The seal of claim 12 wherein said fluid is a gas.

15. The seal of claim 12 wherein said means comprises a channel with an opening into the defined volume.

16. An apparatus for testing gas permeability of plastic bottles, the apparatus comprising a fluid seal comprising:

a cylinder having an interior wall, a first end, and a second end, the ends being open; a plug having a surface said plug disposed in said first end of said cylinder in such manner that a gap exists between the surface of the plug and the interior wall of the cylinder;

a first seal disposed within said gap proximate to said first end, and a second seal disposed within said gap proximate to said second end, said seals, said wall, and said plug surface defining a volume; and, a means provided within said plug permitting introduction and removal of fluid within said defined volume.

* * * * *

UNITED STATES PATENT AND TRADEMARK OFFICE
CERTIFICATE OF CORRECTION

PATENT NO. : 6,598,463 B2
DATED : July 29, 2003
INVENTOR(S) : Sharp Kenneth George et al.

It is certified that error appears in the above-identified patent and that said Letters Patent is hereby corrected as shown below:

Title page,
Insert Item:
-- [73] Assignee: E.I. duPont de Nemours & Company --

Signed and Sealed this

Sixth Day of July, 2004

JON W. DUDAS
*Acting Director of the United States Patent and Trademark Office*